US012716897B2

(12) United States Patent
Xu

(10) Patent No.: US 12,716,897 B2
(45) Date of Patent: Aug. 25, 2026

(54) METHODS AND COMPOSITIONS FOR MONITORING CELLULAR MEMBRANES OR CELLULAR MEMBRANE COATED NANOPARTICLES

(71) Applicant: CELLICS THERAPEUTICS, INC., San Diego, CA (US)

(72) Inventor: Weidong Xu, San Diego, CA (US)

(73) Assignee: CELLICS THERAPEUTICS, INC., San Diego, CA (US)

( * ) Notice: Subject to any disclaimer, the term of this patent is extended or adjusted under 35 U.S.C. 154(b) by 1278 days.

(21) Appl. No.: 16/963,785

(22) PCT Filed: Jan. 24, 2019

(86) PCT No.: PCT/US2019/014998
§ 371 (c)(1),
(2) Date: Jul. 21, 2020

(87) PCT Pub. No.: WO2019/147845
PCT Pub. Date: Aug. 1, 2019

(65) Prior Publication Data

US 2021/0048441 A1 Feb. 18, 2021

Related U.S. Application Data

(60) Provisional application No. 62/622,729, filed on Jan. 26, 2018.

(51) Int. Cl.
*G01N 33/68* (2006.01)
*A61K 9/50* (2006.01)
*A61K 9/51* (2006.01)

(52) U.S. Cl.
CPC ....... *G01N 33/6848* (2013.01); *A61K 9/5068* (2013.01); *A61K 9/5176* (2013.01)

(58) Field of Classification Search
CPC ........ A61K 2039/55555; A61K 9/5153; A61K 9/5068; A61K 9/5176; C07C 16/18; C07K 16/18; G01N 33/6848; C07J 16/18
See application file for complete search history.

(56) References Cited

U.S. PATENT DOCUMENTS 5,843,440 A 12/1998 Pouletty et al.
2013/0337066 A1 12/2013 Zhang et al.

FOREIGN PATENT DOCUMENTS

WO WO-2009117370 A1 * 9/2009 ....... G01N 33/54313
WO 2016028965 A1 2/2016

OTHER PUBLICATIONS

Hu et al. PNAS, 108, 27, 2011, 10980-10985.*
Zaccaria et al. Int J Nanomedicine, 2015, 10, 1869-1883.*
Akker et al., Blood Cells, Molecules and Disease, 45, 2010, 1-8.*
Fye et al., Clin Proteom, 2018, 15(14), 1-8.*
Martel et al. Analytical Biochemistry, 418, 2011, 111-125.*
Grebe et al. Clin Biochem Rev vol. 32, 2011, 5-31.*
Gnjatic et al., J Immunotherapy of Cancer, 2017, 5:44, 1-18.*
Bosman et al., J Proteomics, 2010, 73, 396-402.*
Farrah T, Deutsch EW, Omenn GS, Campbell DS, Sun Z, et al. A high-confidence human plasma proteome reference set with estimated concentrations in Peptide Atlas. Mol Cell Proteomics. 2011;10(9):M110.006353.
Liu X, Valentine SJ, Plasencia MD, Trimpin S, Naylor S, Clemmer DE. Mapping the human plasma proteome by SCX-LC-IMS-MS. J Am Soc Mass Spectrom. 2007; 18(7):1249-64.
Goodman, SR, Krebs KE, Whitfield CF, Riederer BM, and Zagon IS. Spectrin and related molecules. Crit. Rev. Biochem. 1988; 23, 171-234.
Pennell RB. In: Surgenor DM, editor. The red blood cell. New York: Academic Press; 1974. p. 93-146 (preface only).
Kakhniashvili DG, Bulla Jr LA. and Goodman SR. The Human Erythrocyte Proteome Analysis by lon Trap Mass Spectrometry. Molecular & Cellular Proteomics, 2004; 3: 501-509.
Pasini EM, Kirkegaard M, Mortensen P, Lutz HU, Thomas AW. and Mann M. In-depth analysis of the membrane and cytosolic proteome of red blood cells. Blood 2006; 108:791-801.
Pasinia EM, Lutz HU, Mannc M, Thomas AW. Red blood cell (RBC) membrane proteomics—Part I: Proteomics and RBC physiology Journal of Proteomics 2010; 73 (3): 403-420.
Pasini EM, Lutz HU, Mann M, Thomas AW. Red blood cell (RBC) membrane proteomics—Part II: Comparative proteomics and RBC patho-physiology. J Proteomics. 2010; 73(3):421-35.
Shevchenko, A., Wilm, M., Vorm, O., Mann, M. Mass spectrometric sequencing of proteins silver-stained polyacrylamide gels. Anal Chem. 1996; 68(5): 850-8.
International Search Report for international patent application PCT/US2019/14998 (WO2019147845), dated Aug. 1, 2019, 3 pages.
Written Opinion of the International Searching Authority for international patent application PCT/US2019/14998 (WO2019147845), dated Aug.1, 2019, 5 pages.
International Preliminary Report on Patentability for international patent application PCT/US2019/14998 (WO2019147845), dated Jul. 28, 2020, 6 pages.
Kontos et al., "Improving Protein Pharmacokinetics by Engineering Erythrocyte Affinity," Molecular Pharmaceutics, vol. 7, No. 6, P2141-2147, Sep. 10, 2010 DOI: 10.1021/mp1001697.

* cited by examiner

*Primary Examiner* — Kyle A Purdy

(57) ABSTRACT

The present invention relates to methods and compositions for monitoring a cellular membrane or a cellular membrane coated nanoparticle after in vivo administration.

20 Claims, 6 Drawing Sheets

Figure 1:
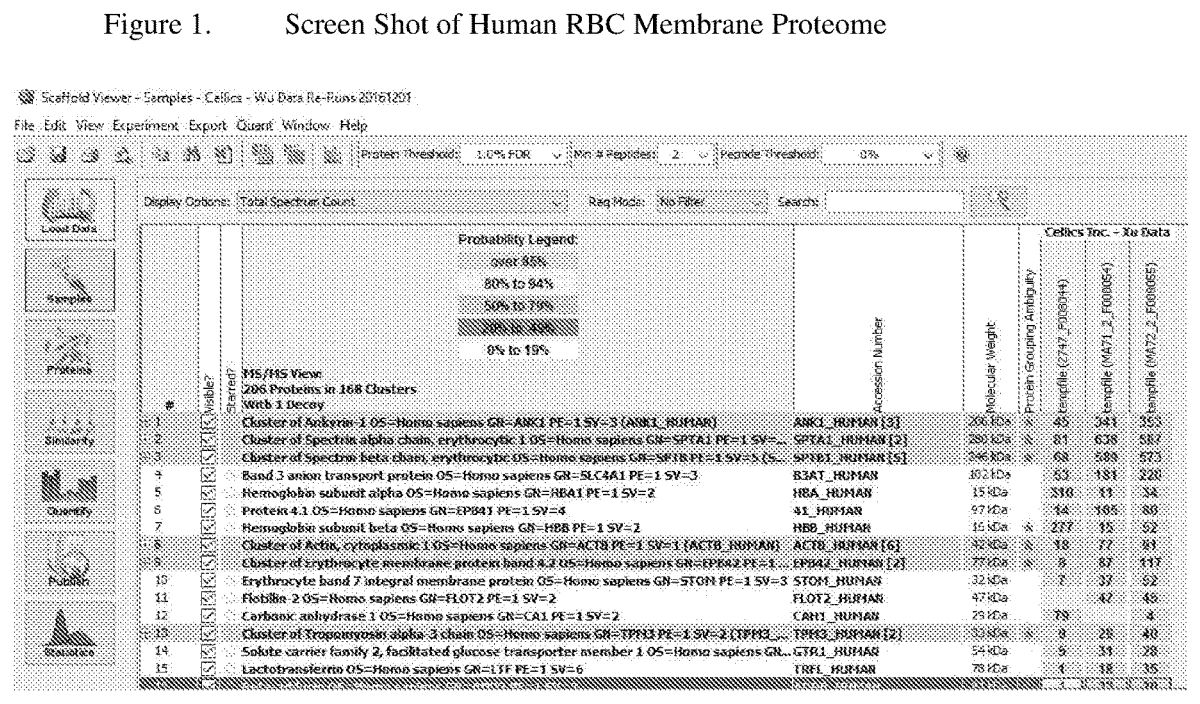

Figure 1. Screen Shot of Human RBC Membrane Proteome

Scaffold Viewer - Samples - Cellics - Wu Data Re-Runs 20161201

File Edit View Experiment Export Quant Window Help

Protein Threshold: 1.0% FDR | Min # Peptides: 2 | Peptide Threshold: 0%

Load Data | Samples | Proteins | Similarity | Quantify | Publish | Statistics

Display Options: Total Spectrum Count | Req Mode: No Filter | Search:

Probability Legend: over 95% | 80% to 94% | 50% to 79% | 20% to 49% | 0% to 19%

MS/MS View:
206 Proteins in 168 Clusters
With 1 Decoy

| # | Visible? | Starred? | Protein | Accession Number | Molecular Weight | Protein Grouping Ambiguity | Cellics Inc. - Xu Data: tempfile (2747_F008044) | tempfile (MA71_2_F008054) | tempfile (MA72_2_F008055) |
|---|---|---|---|---|---|---|---|---|---|
| 1 | ☑ | | Cluster of Ankyrin-1 OS=Homo sapiens GN=ANK1 PE=1 SV=3 (ANK1_HUMAN) | ANK1_HUMAN [3] | 206 kDa | * | 45 | 341 | 353 |
| 2 | ☑ | | Cluster of Spectrin alpha chain, erythrocytic 1 OS=Homo sapiens GN=SPTA1 PE=1 SV=... | SPTA1_HUMAN [2] | 280 kDa | * | 81 | 638 | 587 |
| 3 | ☑ | | Cluster of Spectrin beta chain, erythrocytic OS=Homo sapiens GN=SPTB PE=1 SV=5 (S... | SPTB1_HUMAN [5] | 246 kDa | * | 68 | 589 | 573 |
| 4 | ☑ | | Band 3 anion transport protein OS=Homo sapiens GN=SLC4A1 PE=1 SV=3 | B3AT_HUMAN | 102 kDa | | 53 | 181 | 220 |
| 5 | ☑ | | Hemoglobin subunit alpha OS=Homo sapiens GN=HBA1 PE=1 SV=2 | HBA_HUMAN | 15 kDa | | 310 | 11 | 34 |
| 6 | ☑ | | Protein 4.1 OS=Homo sapiens GN=EPB41 PE=1 SV=4 | 41_HUMAN | 97 kDa | | 14 | 105 | 80 |
| 7 | ☑ | | Hemoglobin subunit beta OS=Homo sapiens GN=HBB PE=1 SV=2 | HBB_HUMAN | 16 kDa | * | 277 | 15 | 52 |
| 8 | ☑ | | Cluster of Actin, cytoplasmic 1 OS=Homo sapiens GN=ACTB PE=1 SV=1 (ACTB_HUMAN) | ACTB_HUMAN [6] | 42 kDa | * | 18 | 77 | 81 |
| 9 | ☑ | | Cluster of Erythrocyte membrane protein band 4.2 OS=Homo sapiens GN=EPB42 PE=1... | EPB42_HUMAN [2] | 77 kDa | * | 8 | 87 | 117 |
| 10 | ☑ | | Erythrocyte band 7 integral membrane protein OS=Homo sapiens GN=STOM PE=1 SV=3 | STOM_HUMAN | 32 kDa | | 7 | 37 | 52 |
| 11 | ☑ | | Flotillin-2 OS=Homo sapiens GN=FLOT2 PE=1 SV=2 | FLOT2_HUMAN | 47 kDa | | | 47 | 48 |
| 12 | ☑ | | Carbonic anhydrase 1 OS=Homo sapiens GN=CA1 PE=1 SV=2 | CAH1_HUMAN | 29 kDa | | 78 | | 4 |
| 13 | ☑ | | Cluster of Tropomyosin alpha-3 chain OS=Homo sapiens GN=TPM3 PE=1 SV=2 (TPM3_... | TPM3_HUMAN [2] | 33 kDa | * | 8 | 28 | 40 |
| 14 | ☑ | | Solute carrier family 2, facilitated glucose transporter member 1 OS=Homo sapiens GN... | GTR1_HUMAN | 54 kDa | | 6 | 31 | 28 |
| 15 | ☑ | | Lactotransferrin OS=Homo sapiens GN=LTF PE=1 SV=6 | TRFL_HUMAN | 78 kDa | | 4 | 18 | 35 |

Figure 2. Western blot analysis of human Band 3 protein
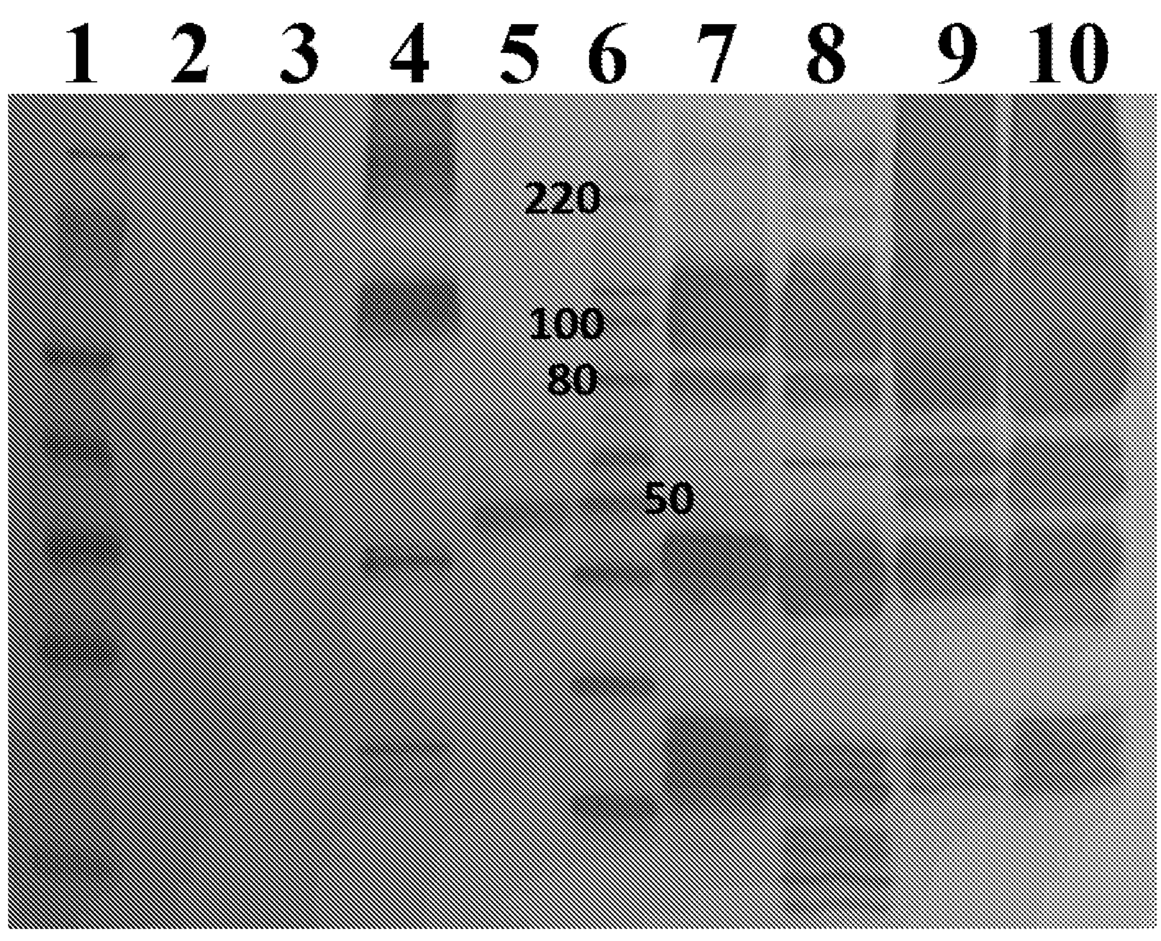

Figure 3. Analysis of human Band 3 protein in the plasma of the mice treated with human Nnnosponge
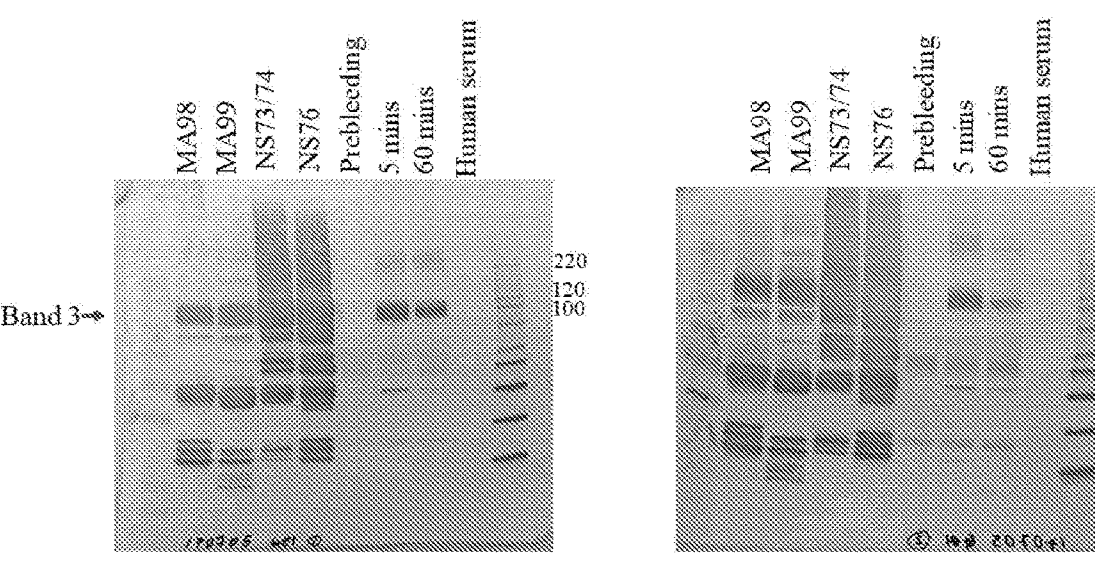
Animal ID: 0999
Animal ID: 1000

Figure 4. Example of human Ankyrin-1 shown in Plasma proteome database
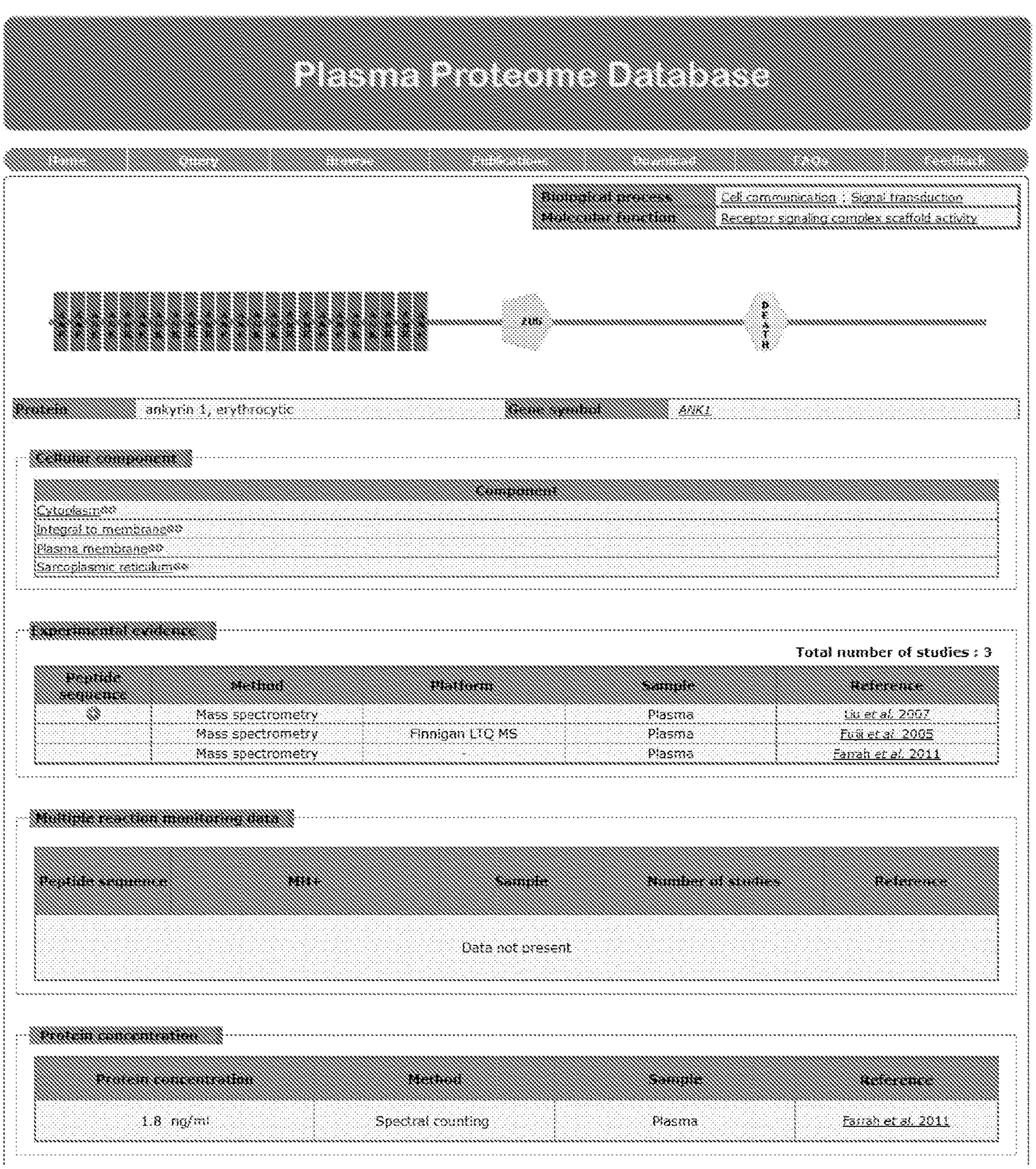

Figure 5. LC/MS/MS quantification of human band 3 peptide A (ADFLEQPVLGFVR)
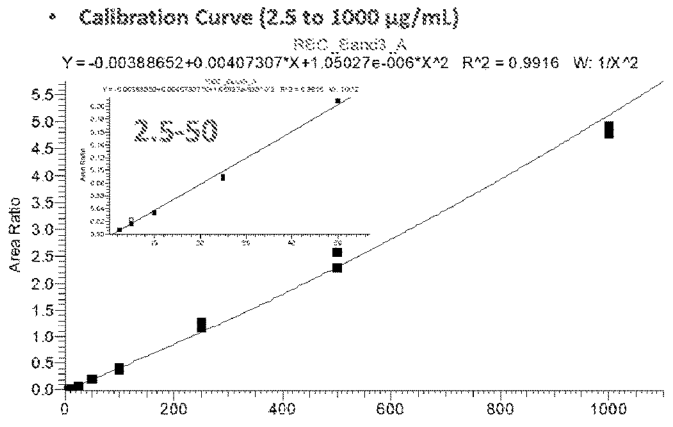
• Calibration Curve Precision and Accuracy
| Norminal Concentration (µg/mL) | Measured Concentration (µg/mL) | Bias | CV |
|---|---|---|---|
| 2.5 | 2.67 | 7% | 4.8% |
| | 2.49 | 0% | |
| 5 | 4.93 | -1% | 0.0% |
| | 6.42 | 28% | |
| 10 | 9.02 | -10% | 1.9% |
| | 9.27 | -7% | |
| 25 | 22.11 | -12% | 3.2% |
| | 23.12 | -8% | |
| 50 | 51.66 | 3% | 0.3% |
| | 51.45 | 3% | |
| 100 | 92.54 | -7% | 8.6% |
| | 104.46 | 4% | |
| 250 | 269.82 | 8% | 5.3% |
| | 290.92 | 16% | |
| 500 | 554.66 | 11% | 7.3% |
| | 500.01 | 0% | |
| 1000 | 969.55 | -3% | 2.0% |
| | 942.50 | -6% | |

Figure 6. LC/MS/MS quantification of human band 3 peptide B (LQEAAELEAVELPVPIR)

- Calibration Curve (5 to 1000 µg/mL)

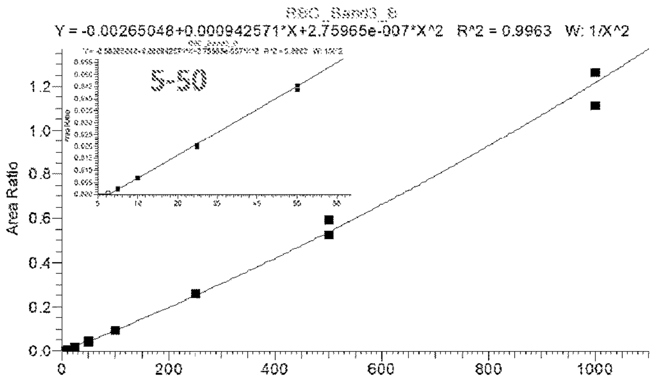

- Calibration Curve Precision and Accuracy

| Norminal Concentration (µg/mL) | Measured Concentration (µg/mL) | Bias | CV |
|---|---|---|---|
| 5 | 4.73 | -5% | 9.5% |
| | 5.41 | 8% | |
| 10 | 10.01 | 0% | 1.1% |
| | 9.86 | -1% | |
| 25 | 23.33 | -7% | 2.6% |
| | 24.19 | -3% | |
| 50 | 50.31 | 1% | 2.7% |
| | 48.43 | -3% | |
| 100 | 100.03 | 0% | 0.7% |
| | 101.09 | 1% | |
| 250 | 257.39 | 3% | 0.2% |
| | 258.12 | 3% | |
| 500 | 544.17 | 9% | 7.4% |
| | 490.29 | -2% | |
| 1000 | 930.04 | -7% | 7.3% |
| | 1030.83 | 3% | |

Figure 7. Tryptic peptides monitored by LC-MS/MS

- Human RBC Membrane Band 3:
  - A. ADFLEQPVLGFVR (aa 234-246)_ Parent Ion, m/z,745.90 (+2); Daughter Ion, m/z 787.47 (y7)
  - B. LQEAAELEAVELPVPIR (aa 247-263)_Parent Ion, m/z 939.02(+2); Daughter Ion, m/z 581.37 (y5)
- BSA_IS peptide:
  - HPYFYAPELLYYANK (aa 169-183) _Parent Ion, m/z 944.97 (+2); Daughter Ion, m/z 935.396(b15)

METHODS AND COMPOSITIONS FOR MONITORING CELLULAR MEMBRANES OR CELLULAR MEMBRANE COATED NANOPARTICLES

I. CROSS-REFERENCE TO RELATED APPLICATION

The present application is a U.S. national phase filing of International Patent Application Serial No. PCT/US2019/014998, filed on Jan. 24, 2019, entitled "Methods and Compositions for Monitoring Cellular Membranes or Cellular Membrane Coated Nanoparticles," which claims priority to U.S. provisional patent application No. 62/622,729, filed on Jan. 26, 2018. The contents and disclosures of the above applications are incorporated herein by reference in their entireties for all purposes.

II. FIELD OF THE INVENTION

The present invention relates to methods and compositions for monitoring a cellular membrane or a cellular membrane coated nanoparticle after in vivo administration.

III. BACKGROUND OF THE INVENTION

Pharmacokinetics (PK) is a branch of pharmacology dedicated to determining the fate of substances administered to a living organism. Toxicokinetics (TK) is the description of both what rate a chemical will enter the body and what occurs to excrete and metabolize the compound once it is in the body. All of those studies need to address drug product concentration inside a living organism, animal or human, and determine the concentration of the drug product in relevant samples, e.g., plasma, serum or urine.

Cellular membrane coated nanoparticles, e.g., human red blood cell membrane nanoparticles, can potentially be used as an active pharmaceutical ingredient (API). New and improved methods and compositions for monitoring cellular membranes or cellular membrane coated nanoparticles after in vivo administration are needed. The present invention addresses these and other related needs in the art.

IV. SUMMARY OF THE INVENTION

In one aspect, the present invention provides a method for monitoring a cellular membrane or a cellular membrane coated nanoparticle after in vivo administration, which method comprises: a) obtaining a sample from a subject to which has been administered a cellular membrane or a cellular membrane coated nanoparticle, said nanoparticle comprising an inner core comprising a non-cellular material and an outer surface comprising a cellular membrane derived from a cell; and b) assessing the presence, absence, amount and/or level of a biomarker from said cellular membrane or cellular membrane of said cellular membrane coated nanoparticle in said sample, said biomarker having a base level in said sample that is below a threshold level.

In another aspect, the present invention provides a kit or system for monitoring a cellular membrane or a cellular membrane coated nanoparticle after in vivo administration, which kit or system comprises: a) means for obtaining a sample from a subject to which has been administered a cellular membrane or a cellular membrane coated nanoparticle, said nanoparticle comprising an inner core comprising a non-cellular material and an outer surface comprising a cellular membrane derived from a cell; and b) means for assessing the presence, absence and/or amount of a biomarker from said cellular membrane or cellular membrane of said cellular membrane coated nanoparticle in said sample, said biomarker having a base level in said sample that is below a threshold level.

V. BRIEF DESCRIPTION OF THE DRAWINGS

FIG. 1 illustrates analysis of human RBC membrane proteome.

FIG. 2 shows, by Western blot, human Band 3 protein was not detected exist in human and animal plasma (lane 2, 3: human and cynomolgus monkey plasma; lane 4: monkey plasma with human nanosponge; lane 5: rat plasma, pinkish color, minor positive detection might be caused by little hemolysis; lane 7, 8: human RBC membrane, MA 98, MA99; lane 9, 10: human nanosponge NS73, NS76).

FIG. 3 illustrates that human Band 3 Protein can be evaluated in the plasma of the mice treated with human nanosponge by western blot. Level of human Band 3 Protein increased in the initial five minutes after human nanosponge administration, then the level decreased at one hour time point in the two different mice.

FIG. 4 illustrates minimal amount of human Ankyrin-1 detected in some of the literatures presented by Plasma Proteome Database.

FIG. 5 illustrates LC/MS/MS quantification of human Band 3 Peptide A (ADFLEQPVLGFVR).

FIG. 6 illustrates LC/MS/MS Quantification of human Band 3 peptide B (LQEAAELEAVELPVPIR).

FIG. 7 illustrates tryptic peptides monitored by LC-MS/MS.

VI. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual,* 2nd ed. (Sambrook et al., 1989); *Oligonucleotide Synthesis* (M. J. Gait, ed., 1984); *Animal Cell Culture* (R. I. Freshney, ed., 1987); Methods in Enzymology (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy,* 20th ed., (Lippincott, Williams & Wilkins 2003), and Josip Lovric, Introducing Proteomics: From Concepts to Sample Separation, Mass Spectrometry and Data Analysis (Wiley; 2011).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 m. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term “pharmaceutically acceptable carrier” as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language “pharmaceutically acceptable carrier” is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20$^{th}$ ed., (Lippincott, Williams & Wilkins 2003). Except insofar as any conventional media or agent is incompatible with the active compound, such use in the compositions is contemplated.

Phospholipid: The term “phospholipid”, as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term “therapeutically effective amount” refers to those amounts that, when administered to a particular subject in view of the nature and severity of that subject’s disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term “therapeutically effective amount” or “effective amount” refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

“Treating” or “treatment” or “alleviation” refers to therapeutic treatment wherein the object is to slow down (lessen) if not cure the targeted pathologic condition or disorder or prevent recurrence of the condition. A subject is successfully “treated” if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term “combination” refers to either a fixed combination in one dosage unit form, or a kit of parts for the combined administration where a nanoparticle or compound and a combination partner (e.g., another drug as explained below, also referred to as “therapeutic agent” or “co-agent”) may be administered independently at the same time or separately within time intervals, especially where these time intervals allow that the combination partners show a cooperative, e.g., synergistic effect. The terms “co-administration” or “combined administration” or the like as utilized herein are meant to encompass administration of the selected combination partner to a single subject in need thereof (e.g., a patient), and are intended to include treatment regimens in which the agents are not necessarily administered by the same route of administration or at the same time. The term “pharmaceutical combination” as used herein means a product that results from the mixing or combining of more than one active ingredient and includes both fixed and non-fixed combinations of the active ingredients. The term “fixed combination” means that the active ingredients, e.g., a nanoparticle or compound and a combination partner, are both administered to a patient simultaneously in the form of a single entity or dosage. The term “non-fixed combination” means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000, 2,000, 3,000, 4,000, 5,000, or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications and/or mutations known in the art.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "epitope" refers to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

As used herein, the term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, at least 6, at least 7, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

An "immunoconjugate" is an antibody conjugated to one or more heterologous molecule(s), including but not limited to a gold particle, a fluorescent dye or particle, quantum dots, and latex or any other labels, for example, for use in ELISA or lateral flow assays. In some embodiments, the antibody is or is part of an immunoconjugate, in which the antibody is conjugated to one or more heterologous molecule(s).

Conjugates of an antibody and one or more heterologous molecule(s) may be made using any of a number of known protein coupling agents, e.g., linkers, (see Vitetta et al., *Science* 238:1098 (1987)), WO94/11026. The linker may be a "cleavable linker," such as acid-labile linkers, peptidase-sensitive linkers, photolabile linkers, dimethyl linkers, and disulfide-containing linkers (Chari et al., *Cancer Res.* 52:127-131 (1992); U.S. Pat. No. 5,208,020).

An "isolated" polypeptide, e.g., isolated antibody, is one which has been separated from a component of its natural environment. In some embodiments, a polypeptide, e.g., an antibody, is purified to greater than 10%, 20%, 30%, 40%, 50%, 60%, 70%, 80%, 90%, 91%, 92%, 93%, 94%, 95%, 96%, 97%, 98%, 99%, 99.9%, 99.99%, 99.999%, or more purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of polypeptide, e.g., antibody, purity, see, e.g., Flatman et al., *J. Chromatogr. B* 848:79-87 (2007).

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, a "sample" can be a solution, a suspension, liquid, powder, a paste, aqueous, non-aqueous or any combination thereof.

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

The terms "level" or "levels" are used to refer to the presence and/or amount of biomarkers, e.g., a polypeptide, a lipid, a carbohydrate, or a combination thereof, and can be determined qualitatively or quantitatively. In some embodiments, a "qualitative" change in the biomarker level refers to the appearance or disappearance of a biomarker that is not detectable or is present in samples obtained from normal controls. In some embodiments, a "quantitative" change in the levels of one or more biomarker of the profile refers to a measurable increase or decrease in the biomarker levels when compared to a healthy control.

A "healthy control" or "normal control" is a biological sample taken from an individual who does not suffer from a disease, disorder or condition, e.g., infection. A "negative control," is a sample that lacks any of the specific analyte the assay is designed to detect and thus provides a reference baseline for the assay.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In some embodiments, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Monitoring Cellular Membranes or Cellular Membrane Coated Nanoparticles In one aspect, the present invention provides a method for monitoring a cellular membrane or a cellular membrane coated nanoparticle after in vivo administration, which method comprises: a) obtaining a sample from a subject to which has been administered a cellular membrane or a cellular membrane coated nanoparticle, said nanoparticle comprising an inner core comprising a non-cellular material and an outer surface comprising a cellular membrane derived from a cell; and b) assessing the presence, absence, amount and/or level of a biomarker from said cellular membrane or cellular membrane of said cellular membrane coated nanoparticle in said sample, said biomarker having a base level in said sample that is below a threshold level.

The present methods can be used to monitor a cellular membrane or a cellular membrane coated nanoparticle after in vivo administration in any suitable sample. In some embodiments, the sample is derived from a vertebrate. The vertebrate can be a mammal, e.g., a non-human mammal or a human, a bird (Ave), e.g., a chicken, a reptile, e.g., a snake, or a fish. In other embodiments, the sample is derived from vertebrate blood. For example, the sample can be derived from mammalian blood. In another example, the sample can be derived from non-human mammalian blood. In still another example, the sample can be derived from human blood.

In some embodiments, the present methods can be used to monitor a cellular membrane after in vivo administration. The present methods can be used to monitor any suitable cellular membrane, e.g., cellular membrane described in US 2013/337066 A1 or WO 2017/087897 A1, after in vivo administration. The cellular membrane can comprise a plasma membrane or an intracellular membrane. The cellular membrane can be derived from a unicellular organism, e.g., a bacterium or a fungus, or a multicellular organism, e.g., a plant, a vertebrate, a bird (Ave), e.g., a chicken, a reptile, e.g., a snake, a fish, a non-human mammal, or a human. The cellular membrane can also derived from a blood cell, a tumor cell, a cancer cell, an immune cell, a stem cell, an endothelial cell, an exosome, a secretory vesicle or a synaptic vesicle. In an example, the cellular membrane comprises a plasma membrane derived from a red blood cell.

In some embodiments, the present methods can be used to monitor a cellular membrane coated nanoparticle after in vivo administration. The present methods can be used to monitor a cellular membrane coated nanoparticle after in vivo administration in a sample that contains a cellular membrane coated nanoparticle, said nanoparticle comprising an inner core comprising a non-cellular material and an outer surface comprising a cellular membrane derived from a hemoglobin-containing cell. The present methods can be used to monitor any suitable cellular membrane coated nanoparticle, e.g., cellular membrane coated nanoparticle described in US 2013/337066 A1 or WO 2017/087897 A1, after in vivo administration. In some embodiments, the inner core of the nanoparticle can comprise a biocompatible and/or a synthetic material, such as poly(lactic-c-glycolic acid) (PLGA), polylactic acid (PLA), polyglycolic acid (PGA), polycaprolactone (PCL), polylysine, polyglutamic acid, or a hydrophobic polymer that coils when switched from an organic solvent to an aqueous phase, e.g., water. In other embodiments, the inner core of the nanoparticle supports the outer surface.

The cellular membrane of the nanoparticle can comprise a plasma membrane or an intracellular membrane. The cellular membrane of the nanoparticle can be derived from a unicellular organism, e.g., a bacterium or a fungus, or a multicellular organism, e.g., a plant, a vertebrate, a bird (Ave), e.g., a chicken, a reptile, e.g., a snake, a fish, a non-human mammal, or a human. The cellular membrane of the nanoparticle can also be derived from a blood cell, a tumor cell, a cancer cell, an immune cell, a stem cell, an endothelial cell, an exosome, a secretory vesicle or a synaptic vesicle. In an example, the cellular membrane comprises a plasma membrane derived from a red blood cell.

In some embodiments, the nanoparticle does not comprise a releasable cargo. In other embodiments, the nanoparticle further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, an imaging agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 μm, preferably about 50 nm to about 150 nm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 m.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of a cell, e.g., a hemoglobin-containing cell or a red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of a cell, e.g., a hemoglobin-containing cell or a red blood cell, from which the cellular membrane is derived. In some embodiments, the nanoparticle comprises a plasma membrane derived from a hemoglobin-containing cell, e.g., a red blood cell, and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular membrane or the constituents of the cellular membrane including primary, secondary, tertiary and/or quaternary structure of the cellular membrane, or the constituents of the cellular membrane. In some embodiments, the nanoparticle substantially maintains activity of the cellular membrane or the constituents of the cellular membrane including binding activity, receptor activity and/or enzymatic activity of the cellular membrane, or the constituents of the cellular membrane.

In some embodiments, the nanoparticle is biocompatible or biodegradable. For example, the inner core of the nanoparticle comprises PLGA and the outer surface of the nanoparticle comprises a plasma membrane derived from a cell, e.g., a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the nanoparticle substantially lacks immunogenicity to a subject, a mammal, a non-human mammal or a human, to which the nanoparticle is configured to administer. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to which the nanoparticle is configured to administer.

The outer surface of the nanoparticle can comprise a hybrid membrane comprising a cellular membrane derived from a cell and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane and about 95-99%

(w/w) of a synthetic membrane, about 11-25% (w/w) of a cellular membrane and about 75-89% (w/w) of a synthetic membrane, about 50% (w/w) of a cellular membrane and about 50% (w/w) of a synthetic membrane, about 51-75% (w/w) of a cellular membrane and about 49-25% (w/w) of a synthetic membrane, or about 90-99% (w/w) of a cellular membrane and about 1-10% (w/w) of a synthetic membrane.

The presence, absence and/or amount of a biomarker can be assessed by any suitable assay. For example, the presence, absence and/or amount of a biomarker can be assessed by an immunoassay, a chromatography analysis, a mass spectrometry analysis, a proteomics analysis, or a combination thereof.

In some embodiments, the presence, absence and/or amount of a biomarker can be assessed by an immunoassay. Exemplary immunoassays include an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

In some embodiments, the presence, absence and/or amount of a biomarker can be assessed by chromatography analysis. Exemplary chromatography analyses include liquid chromatography, e.g., adsorption chromatography, partition chromatography, ion chromatography, size-exclusion chromatography or affinity chromatography. Exemplary chromatography analysis also includes a high-performance liquid chromatography (HPLC or high-pressure liquid chromatography).

In some embodiments, the presence, absence and/or amount of a biomarker can be assessed by liquid chromatography-mass spectrometry (LC-MS) analysis or liquid chromatography-mass spectrometry-mass spectrometry (LC-MS-MS) analysis. Any suitable LC/MS analysis or LC/MS/MS analysis can be used. For example, the LC/MS analysis or LC/MS/MS analysis can employ an interface that transfers separated components from the LC column into the MS ion source. Any suitable interface can be used. For example, the interface can be based on atmospheric pressure ionization (API), e.g., electrospray ionization (ESI), atmospheric pressure chemical ionization (APCI), or atmospheric pressure photo-ionization (APPI).

In some embodiments, the presence, absence and/or amount of a biomarker can be assessed by a mass spectrometry analysis. Exemplary mass spectrometry analyses include matrix-assisted laser desorption/ionization (MALDI)-time of flight (TOF), inductively coupled plasma mass spectrometry (ICP-MS), accelerator mass spectrometry (AMS), thermal ionization mass spectrometry (TIMS), or spark source mass spectrometry (SSMS).

In some embodiments, the present methods can be used to assess the presence or absence of a biomarker from a cellular membrane or a cellular membrane coated nanoparticle in a sample. In other embodiments, the present methods can be used to assess the amount of a biomarker from a cellular membrane or a cellular membrane coated nanoparticle in a sample.

The cellular membrane or cellular membrane in the nanoparticle can be derived from a cell of a species that is the same as that of the subject to which the cellular membrane or the nanoparticle is to be or has been administered. The cellular membrane or cellular membrane in the nanoparticle can also be derived from a cell of a species that is different from that of the subject to which the cellular membrane or e nanoparticle is to be or has been administered.

Any suitable biomarker can be assessed in the present methods. For example, the biomarker can be a polypeptide, a lipid, a carbohydrate, a fragment thereof, or a combination thereof. In some embodiments, the biomarker can be a polypeptide, a fragment thereof, or fragments thereof. The fragment(s) can have any suitable length, e.g., at least 5, 6, 7, 8, 9, 10, 15, 20, 25, 30, 35, 40, 45, 50, 60, 70, 80, 90, 100, 110, 120, 130, 140, 150, 200, 300, 400, 500, 600, 700, 800, 900, 1,000 or more amino acid residues, or a subrange thereof.

In some embodiments, the biomarker to be assessed in the present methods is Band 3 protein, Spectrin alpha, spectrin beta, ankyrin-1, EPB41 or EPB42, Ankyrin-2, Ankyrin-3, Ankyrin domain family J, Ankyrin domain family E, Erythrocyte band 7 protein, Tropomysin alpha-1, Tropomysin alpha-3, Beta-adducin, or a fragment thereof, or fragments thereof. Each of the Band 3 protein, Spectrin alpha, spectrin beta, ankyrin-1, EPB41, EPB42, Ankyrin-2, Ankyrin-3, Ankyrin domain family J, Ankyrin domain family E, Erythrocyte band 7 protein, Tropomysin alpha-1, Tropomysin alpha-3, Beta-adducin can comprise any suitable amino acid sequence(s) known in the art. For example, Band 3 protein can comprise an amino acid sequence set forth in GenBank Accession or UniProtKB/Swiss-Prot No. CAP46016 or P02730, Spectrin alpha can comprise an amino acid sequence set forth in GenBank Accession or UniProtKB/Swiss-Prot No. P02549, spectrin beta can comprise an amino acid sequence set forth in GenBank Accession or UniProtKB/Swiss-Prot No. P11277, ankyrin-1 can comprise an amino acid sequence set forth in GenBank Accession or UniProtKB/Swiss-Prot No. P16157, EPB41 can comprise an amino acid sequence set forth in GenBank Accession or UniProtKB/Swiss-Prot No. P11171, EPB42 can comprise an amino acid sequence set forth in GenBank Accession or UniProtKB/Swiss-Prot No. P16452, Ankyrin-2 can comprise an amino acid sequence set forth in GenBank Accession or UniProtKB/Swiss-Prot No. Q01484, Ankyrin-3 can comprise an amino acid sequence set forth in GenBank Accession or UniProtKB/Swiss-Prot No. Q12955, Ankyrin domain family J can comprise an amino acid sequence set forth in GenBank Accession or UniProtKB/Swiss-Prot No. POCG39, Ankyrin domain family E can comprise an amino acid sequence set forth in GenBank Accession or UniProtKB/Swiss-Prot No. Q6S8J3, Erythrocyte band 7 protein can comprise an amino acid sequence set forth in GenBank Accession or UniProtKB/Swiss-Prot No. P27105, Tropomysin alpha-1 can comprise an amino acid sequence set forth in GenBank Accession or UniProtKB/Swiss-Prot No. P09493, Tropomysin alpha-3 can comprise an amino acid sequence set forth in GenBank Accession or UniProtKB/Swiss-Prot No. P06753, and Beta-adducin can comprise an amino acid sequence set forth in GenBank Accession or UniProtKB/Swiss-Prot No. P35612.

In some embodiments, the biomarker to be assessed in the present methods is Band 3 protein, a fragment thereof, or fragments thereof.

The cellular membrane or cellular membrane of the nanoparticle can comprise a plasma membrane derived from any suitable cell. For example, the cellular membrane or cellular membrane of the nanoparticle can comprise a plasma membrane derived from a red blood cell, e.g., human or non-human mammalian red blood cell.

The cellular membrane of the nanoparticle can comprise a plasma membrane derived from a red blood cell of any suitable species. For example, the cellular membrane of the nanoparticle can comprise a plasma membrane derived from a red blood cell of a species that is the same as that of the subject to which the nanoparticle is to be or has been administered. In another example, the cellular membrane of the nanoparticle comprises a plasma membrane derived from a human red blood cell and the nanoparticle is administered to a human. In still another example, the cellular membrane of the nanoparticle comprises a plasma membrane derived from a red blood cell of a non-human mammal and the nanoparticle is administered to same species of the non-human mammal. In yet another example, the cellular membrane of the nanoparticle comprises a plasma membrane derived from a human red blood cell and the nanoparticle is administered to a non-human mammal. Exemplary non-human mammal can be a mouse, a rat, a monkey, a dog, a rabbit, or a Gennie pig.

In the present methods, the base level of the biomarker can be at any suitable level. For example, the base level of the biomarker, e.g., Band 3 protein, in the sample can be about 5 ng/ml, e.g., 5 ng Band 3 protein/ml plasma or serum, or less.

In some embodiments, the nanoparticle, other than the biomarker, does not comprise an additional marker or label to facilitate or enable monitoring of the nanoparticle after in vivo administration. In other embodiments, the nanoparticle, other than the biomarker, comprises an additional marker or label to facilitate or enable monitoring of the nanoparticle after in vivo administration. Any suitable label can be used, e.g., a colormetric, fluorescent or radioactive label.

The present methods can be used to monitor the cellular membrane or the nanoparticle, after in vivo administration, for any suitable time. For example, The present methods can be used to monitor the cellular membrane or the nanoparticle, after in vivo administration, for a time ranging from about 1 minute to about 1 month, e.g., about 1 minute, 5 minutes, 10 minutes, 15 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 month or longer, or a subrange thereof.

The present methods can be used for any suitable purpose. In some embodiments, the present methods can be used to monitor the cellular membrane or the nanoparticle in a quality control (QC) test or quality assurance (QA) test, e.g., in a process for manufacturing or inspecting the nanoparticle. In other embodiments, the present methods can be used to monitor the cellular membrane or the nanoparticle in a pharmacology study or in a toxicology study.

The present methods can be used to monitor the cellular membrane or the nanoparticle in any suitable pharmacology study. For example, the pharmacology study can be a pharmacodynamics study or a pharmacokinetics study. In some embodiments, the pharmacokinetics study is used to assess liberation, absorption, distribution, metabolism and/or elimination (or excretion) of the cellular membrane or the nanoparticle in a subject. In other embodiments, the pharmacokinetics study is used to assess dose, dosing interval, $C_{max}$, $t_{max}$, $C_{min}$, volume of distribution, concentration, biological half-life or terminal half-life, elimination rate constant, infusion rate, area under the curve, clearance, bioavailability and/or fluctuation of the cellular membrane or the nanoparticle in a subject. In still other embodiments, the pharmacodynamics study is used to assess effect(s) of the cellular membrane or the nanoparticle on the body of a subject. In yet other embodiments, the pharmacodynamics study is used to assess desired activity, undesirable effect(s), therapeutic window and/or duration of action of the cellular membrane or the nanoparticle in a subject. In yet other embodiments, the pharmacodynamics study is used to assess receptor binding and effect of the cellular membrane or the nanoparticle in a subject.

The present methods can be used to monitor the cellular membrane or the nanoparticle in any suitable toxicology study. For example, the toxicology study can be used to assess an adverse effect of the cellular membrane or the nanoparticle in a subject due to route of exposure and/or dose (duration and concentration of exposure).

The present methods can be used to monitor the cellular membrane or the nanoparticle in a pre-clinical study. The present methods can also be used to monitor the cellular membrane or the nanoparticle in a clinical study. The clinical study can be a phase I, II, III or post-approval study.

The ratio between the level of a biomarker in a sample obtained from a subject to which has been administered the cellular membrane or the nanoparticle and the base level of the biomarker in the sample can be any suitable number. For example, a ratio between the level of a biomarker in a sample obtained from a subject to which has been administered the cellular membrane or the nanoparticle and the base level of the biomarker in the sample can be at least 2, e.g., at least 3, 4, 5, 6, 7, 8, 9, 10, 20, 30, 40, 50, 60, 70, 80, 90, 100, 200, 300, 400, 500, 600, 700, 800, 900, 1,000, or higher.

In some embodiments, the cellular membrane or the cellular membrane of the nanoparticle comprises a plasma membrane derived from a human red blood cell, the biomarker is Band 3 protein, a fragment or fragments thereof, the subject is a mammal, e.g., a human or a non-human mammal, and the sample is a blood sample, e.g., plasma or serum. The amount and/or level of Band 3 protein, a fragment or fragments thereof can be assessed by an immunoassay, e.g., ELISA. With the immunoassay, e.g., ELISA, the present methods can have an assay linearity ranging from 100 pg Band 3 protein/ml sample, e.g., serum to about 100 ng Band 3 protein/ml sample, e.g., serum, a relative standard deviation (RSD) of 30% or less, and/or a limit of detection (LOD) of Band 3 protein at about 50 or 100 pg Band 3 protein/ml sample, e.g., serum. The amount and/or level of Band 3 protein, a fragment or fragments thereof can be assessed by LC/MS/MS analysis. With the LC/MS/MS analysis, the present methods can have an assay linearity ranging from 1 μg cellular membrane coated nanoparticle/ml sample, e.g., serum to about 1,000 μg cellular membrane coated nanoparticle/ml sample, e.g., serum, a relative standard deviation (RSD) of 20% or less, and/or a limit of detection (LOD) of Band 3 protein at about 1 μg cellular membrane coated nanoparticle/ml sample.

In some embodiments, the present methods further comprise administering the cellular membrane or the cellular membrane coated nanoparticle to the subject.

C. Kits or Systems for Monitoring Cellular Membranes or Cellular Membrane Coated Nanoparticles In another aspect, the present invention provides a kit or system for monitoring a cellular membrane or a cellular membrane coated nanoparticle after in vivo administration, which kit or system comprises: a) means for obtaining a sample from a subject to which has been administered a cellular membrane or a cellular membrane coated nanoparticle, said nanoparticle comprising an inner core comprising a non-cellular material and an outer surface comprising a cellular membrane derived from a cell; and b) means for assessing the presence, absence and/or amount of a biomarker from said cellular membrane or cellular membrane of said cellular membrane coated nanoparticle in said sample, said biomarker having a base level in said sample that is below a threshold level.

The present kits or systems can be used to monitor a cellular membrane or a cellular membrane coated nanoparticle after in vivo administration in any suitable sample. In some embodiments, the sample is derived from a vertebrate. The vertebrate can be a mammal, e.g., a non-human mammal or a human, a bird (Ave), e.g., a chicken, a reptile, e.g., a snake, or a fish. In other embodiments, the sample is derived from vertebrate blood. For example, the sample can be derived from mammalian blood. In another example, the sample can be derived from non-human mammalian blood. In still another example, the sample can be derived from human blood.

In some embodiments, the present kits or systems can be used to monitor a cellular membrane after in vivo administration. The present kits or systems can be used to monitor any suitable cellular membrane after in vivo administration. The cellular membrane can comprise a plasma membrane or an intracellular membrane. The cellular membrane can be derived from a unicellular organism, e.g., a bacterium or a fungus, or a multicellular organism, e.g., a plant, a vertebrate, a bird (Ave), e.g., a chicken, a reptile, e.g., a snake, a fish, a non-human mammal, or a human. The cellular membrane can also derived from a blood cell, a tumor cell, a cancer cell, an immune cell, a stem cell, an endothelial cell, an exosome, a secretory vesicle or a synaptic vesicle. In an example, the cellular membrane comprises a plasma membrane derived from a red blood cell.

In some embodiments, the present kits or systems can be used to monitor a cellular membrane coated nanoparticle after in vivo administration. The present kits or systems can be used to monitor a cellular membrane coated nanoparticle after in vivo administration in a sample that contains a cellular membrane coated nanoparticle, said nanoparticle comprising an inner core comprising a non-cellular material and an outer surface comprising a cellular membrane derived from a hemoglobin-containing cell. The present kits or systems can be used to monitor any suitable cellular membrane coated nanoparticle after in vivo administration. In some embodiments, the inner core of the nanoparticle can comprise a biocompatible and/or a synthetic material, such as poly(lactic-c-glycolic acid) (PLGA), polylactic acid (PLA), polyglycolic acid (PGA), polycaprolactone (PCL), polylysine, polyglutamic acid, or a hydrophobic polymer that coils when switched from an organic solvent to an aqueous phase, e.g., water. In other embodiments, the inner core of the nanoparticle supports the outer surface.

The cellular membrane of the nanoparticle can comprise a plasma membrane or an intracellular membrane. The cellular membrane of the nanoparticle can be derived from a unicellular organism, e.g., a bacterium or a fungus, or a multicellular organism, e.g., a plant, a vertebrate, a bird (Ave), e.g., a chicken, a reptile, e.g., a snake, a fish, a non-human mammal, or a human. The cellular membrane of the nanoparticle can also be derived from a blood cell, a tumor cell, a cancer cell, an immune cell, a stem cell, an endothelial cell, an exosome, a secretory vesicle or a synaptic vesicle. In an example, the cellular membrane comprises a plasma membrane derived from a red blood cell.

In some embodiments, the nanoparticle does not comprise a releasable cargo. In other embodiments, the nanoparticle further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, an imaging agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 μm, preferably about 50 nm to about 150 nm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 m, 2 μm, 3 μm, 4 μm, 5 μm, 6 μm, 7 μm, 8 μm, 9 μm, and 10 m.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of a cell, e.g., a hemoglobin-containing cell or a red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of a cell, e.g., a hemoglobin-containing cell or a red blood cell, from which the cellular membrane is derived. In some embodiments, the nanoparticle comprises a plasma membrane derived from a hemoglobin-containing cell, e.g., a red blood cell, and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular membrane or the constituents of the cellular membrane including primary, secondary, tertiary and/or quaternary structure of the cellular membrane, or the constituents of the cellular membrane. In some embodiments, the nanoparticle substantially maintains activity of the cellular membrane or the constituents of the cellular membrane including binding activity, receptor activity and/ or enzymatic activity of the cellular membrane, or the constituents of the cellular membrane.

In some embodiments, the nanoparticle is biocompatible or biodegradable. For example, the inner core of the nanoparticle comprises PLGA and the outer surface of the nanoparticle comprises a plasma membrane derived from a cell, e.g., a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the nanoparticle substantially lacks immunogenicity to a subject, a mammal, a non-human mammal or a human, to which the nanoparticle is configured to administer. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to which the nanoparticle is configured to administer.

The outer surface of the nanoparticle can comprise a hybrid membrane comprising a cellular membrane derived from a cell and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane and about 95-99% (w/w) of a synthetic membrane, about 11-25% (w/w) of a cellular membrane and about 75-89% (w/w) of a synthetic membrane, about 50% (w/w) of a cellular membrane and about 50% (w/w) of a synthetic membrane, about 51-75% (w/w) of a cellular membrane and about 49-25% (w/w) of a synthetic membrane, or about 90-99% (w/w) of a cellular membrane and about 1-10% (w/w) of a synthetic membrane.

The means for assessing the presence, absence and/or amount of a biomarker from said cellular membrane or cellular membrane of said cellular membrane coated nanoparticle can be any suitable means. For example, the means for assessing the presence, absence and/or amount of a biomarker can be means, e.g., devices, reagents, equipments and/or systems, for conducting an immunoassay, a chromatography analysis, a mass spectrometry analysis, a proteomics analysis, or a combination thereof.

In some embodiments, the means for assessing the presence, absence and/or amount of a biomarker can be means, e.g., devices, reagents, equipments and/or systems, for conducting an immunoassay. Exemplary immunoassays include an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

In some embodiments, the means for assessing the presence, absence and/or amount of a biomarker can be means, e.g., devices, reagents, equipments and/or systems, for conducting a chromatography analysis. Exemplary chromatography analysis includes liquid chromatography, e.g., adsorption chromatography, partition chromatography, ion chromatography, size-exclusion chromatography or affinity chromatography. Exemplary chromatography analysis also includes a high-performance liquid chromatography (HPLC or high-pressure liquid chromatography).

In some embodiments, the means for assessing the presence, absence and/or amount of a biomarker can be means, e.g., devices, reagents, equipments and/or systems, for conducting liquid chromatography-mass spectrometry (LC/MS) analysis or liquid chromatography-mass spectrometry-mass spectrometry (LC/MS/MS) analysis. Any suitable LC/MS analysis or LC/MS/MS analysis can be used. For example, the LC/MS analysis or LC/MS/MS analysis can employ an interface that transfers separated components from the LC column into the MS ion source. Any suitable interface can be used. For example, the interface can be based on atmospheric pressure ionization (API), e.g., electrospray ionization (ESI), atmospheric pressure chemical ionization (APCI), or atmospheric pressure photo-ionization (APPI).

In some embodiments, the means for assessing the presence, absence and/or amount of a biomarker can be means, e.g., devices, reagents, equipments and/or systems, for conducting a mass spectrometry analysis. Exemplary mass spectrometry analyses include matrix-assisted laser desorption/ionization (MALDI)-time of flight (TOF), inductively coupled plasma mass spectrometry (ICP-MS), accelerator mass spectrometry (AMS), thermal ionization mass spectrometry (TIMS), or spark source mass spectrometry (SSMS).

In some embodiments, the present kits or systems can be used to assess the presence or absence of a biomarker from a cellular membrane or a cellular membrane coated nanoparticle in a sample. In other embodiments, the present kits or systems can be used to assess the amount of a biomarker from a cellular membrane or a cellular membrane coated nanoparticle in a sample.

The cellular membrane or cellular membrane in the nanoparticle can be derived from a cell of a species that is the same as that of the subject to which the cellular membrane or the nanoparticle has been administered. The cellular membrane or cellular membrane in the nanoparticle can also be derived from a cell of a species that is different from that of the subject to which the cellular membrane or e nanoparticle has been administered.

Any suitable biomarker can be assessed by the present kits or systems. For example, the biomarker can be a polypeptide, a lipid, a carbohydrate, a fragment thereof, or a combination thereof. In some embodiments, the biomarker can be a polypeptide, a fragment thereof, or fragments thereof. The fragment(s) can have any suitable length, e.g., at least 5, 6, 7, 8, 9, 10, 15, 20, 25, 30, 35, 40, 45, 50, 60, 70, 80, 90, 100, 110, 120, 130, 140, 150, 200, 300, 400, 500, 600, 700, 800, 900, 1,000 or more amino acid residues, or a subrange thereof.

In some embodiments, the biomarker to be assessed by the present kits or systems is Band 3 protein, Spectrin alpha, spectrin beta, ankyrin-1, EPB41, EPB42, Ankyrin-2, Ankyrin-3, Ankyrin domain family J, Ankyrin domain family E, Erythrocyte band 7 protein, Tropomysin alpha-1, Tropomysin alpha-3, Beta-adducin, or a fragment thereof, or fragments thereof. In some embodiments, the biomarker to be assessed by the present kits or systems is Band 3 protein, a fragment thereof, or fragments thereof.

The cellular membrane or cellular membrane of the nanoparticle can comprise a plasma membrane derived from any suitable cell. For example, the cellular membrane or cellular membrane of the nanoparticle can comprise a plasma membrane derived from a red blood cell, e.g., human or non-human mammalian red blood cell.

The cellular membrane of the nanoparticle can comprise a plasma membrane derived from a red blood cell of any suitable species. For example, the cellular membrane of the nanoparticle can comprise a plasma membrane derived from a red blood cell of a species that is the same as that of the subject to which the nanoparticle has been administered. In another example, the cellular membrane of the nanoparticle comprises a plasma membrane derived from a human red blood cell and the nanoparticle is administered to a human. In still another example, the cellular membrane of the nanoparticle comprises a plasma membrane derived from a red blood cell of a non-human mammal and the nanoparticle is administered to same species of the non-human mammal. In yet another example, the cellular membrane of the nanoparticle comprises a plasma membrane derived from a human red blood cell and the nanoparticle is administered to a non-human mammal. Exemplary non-human mammal can be a mouse, a rat, a monkey, a dog, a rabbit, or a Gennie pig.

In some embodiments, the nanoparticle, other than the biomarker, does not comprise an additional marker or label to facilitate or enable monitoring of the nanoparticle after in vivo administration. In other embodiments, the nanoparticle, other than the biomarker, comprises an additional marker or label to facilitate or enable monitoring of the nanoparticle after in vivo administration. Any suitable label can be used, e.g., a colormetric, fluorescent or radioactive label.

The present kits or systems can be used to monitor the cellular membrane or the nanoparticle, after in vivo administration, for any suitable time. For example, The present kits or systems can be used to monitor the cellular membrane or the nanoparticle, after in vivo administration, for a time ranging from about 1 minute to about 1 month, e.g., about 1 minute, 5 minutes, 10 minutes, 15 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 month or longer, or a subrange thereof.

The present kits or systems can be used for any suitable purpose. In some embodiments, the present kits or systems can be used to monitor the cellular membrane or the nanoparticle in a quality control (QC) test or quality assurance (QA) test, e.g., in a process for manufacturing or inspecting the cellular membrane or the nanoparticle. In other embodiments, the present kits or systems can be used to monitor the cellular membrane or the nanoparticle in a pharmacology study or in a toxicology study.

The present kits or systems can be used to monitor the cellular membrane or the nanoparticle in any suitable pharmacology study. For example, the pharmacology study can be a pharmacodynamics study or a pharmacokinetics study. In some embodiments, the pharmacokinetics study is used to assess liberation, absorption, distribution, metabolism and/or elimination (or excretion) of the cellular membrane or the nanoparticle in a subject. In other embodiments, the pharmacokinetics study is used to assess dose, dosing interval, $C_{max}$, $t_{max}$, $C_{min}$, volume of distribution, concentration, biological half-life or terminal half-life, elimination rate constant, infusion rate, area under the curve, clearance, bioavailability and/or fluctuation of the cellular membrane or the nanoparticle in a subject. In still other embodiments, the pharmacodynamics study is used to assess effect(s) of the cellular membrane or the nanoparticle on the body of a subject. In yet other embodiments, the pharmacodynamics study is used to assess desired activity, undesirable effect(s), therapeutic window and/or duration of action of the cellular membrane or the nanoparticle in a subject. In yet other embodiments, the pharmacodynamics study is used to assess receptor binding and effect of the cellular membrane or the nanoparticle in a subject.

The present kits or systems can be used to monitor the cellular membrane or the nanoparticle in any suitable toxicology study. For example, the toxicology study can be used to assess an adverse effect of the cellular membrane or the nanoparticle in a subject due to route of exposure and/or dose (duration and concentration of exposure).

The present kits or systems can be used to monitor the cellular membrane or the nanoparticle in a pre-clinical study. The present kits or systems can also be used to monitor the cellular membrane or the nanoparticle in a clinical study. The clinical study can be a phase I, II, III or post-approval study.

In some embodiments, the cellular membrane of the nanoparticle comprises a plasma membrane derived from a human red blood cell, the biomarker is Band 3 protein, a fragment or fragments thereof, the subject is a mammal, e.g., a human or a non-human mammal, and the sample is a blood sample, e.g., plasma or serum. The amount and/or level of Band 3 protein, a fragment or fragments thereof can be assessed by an immunoassay, e.g., ELISA. With the immunoassay, e.g., ELISA, the present kits or systems can have an assay linearity ranging from 100 μg Band 3 protein/ml sample, e.g., serum to about 100 ng Band 3 protein/ml sample, e.g., serum, a relative standard deviation (RSD) of 30% or less, and/or a limit of detection (LOD) of Band 3 protein at about 50 or 100 pg Band 3 protein/ml sample, e.g., serum. The amount and/or level of Band 3 protein, a fragment or fragments thereof can be assessed by LC-MS-MS analysis. With the LC-MS-MS analysis, the present kits or systems can have an assay linearity ranging from 1 μg cellular membrane coated nanoparticle/ml sample, e.g., serum to about 1,000 μg cellular membrane coated nanoparticle/ml sample, e.g., serum, a relative standard deviation (RSD) of 20 or less, and/or a limit of detection (LOD) of Band 3 protein at about 1 μg cellular membrane coated nanoparticle/ml sample.

In some embodiments, the means for assessing the presence, absence and/or amount of the biomarker comprises a reagent, a device and/or an equipment for assessing the presence, absence and/or amount of the biomarker via an immunoassay, a chromatography analysis, a mass spectrometry analysis, a proteomics analysis, or a combination thereof.

In some embodiments, the present kits or systems can further comprise a cellular membrane or a cellular membrane coated nanoparticle, said nanoparticle comprising an inner core comprising a non-cellular material and an outer surface comprising a cellular membrane derived from a cell.

D. Example

Introduction

In some embodiments, we performed a LC/MS/MS proteomics analysis on our TFF processed human red blood cell membrane. We have identified that four of RBC membrane proteins are uniquely presented in the RBC membrane abundantly. Searching the Plasma Proteome Database (http://plasmaproteomedatabase.org), we have determined that Band 3 in the RBC membrane was not on the list of human plasma proteins and can be used to monitor nanosponge. The other three RBC membrane Spectrin alpha, spectrin beta, ankyrin-1, although reported in the Plasma Proteome Database in the trace amount at 1.2-1.8 ng/ml, may be good candidates for monitoring nanosponge product for PK/TK studies. Several analytical methods, including LC/MS/MS proteomic quantification of specific peptide inside those proteins and immunoassays, such as ELISA, can be used to assess Band 3, Spectrin alpha, spectrin beta, ankyrin-1 from human red blood cell membrane or human red blood cell membrane coated nanoparticles.

Experimental Design and Methods

RBC Membrane and RBC Membrane Coated Nanoparticle Preparation

Red blood cell (RBC) membrane, e.g., human RBC membrane, is generally prepared according to the principles or procedures described in US 2013/337066 A1 or WO 2017/087897 A1. For example, human RBC membrane can be prepared by a process that comprises the steps of lysing red blood cells to obtain a composition comprising RBC membrane and non-membrane cellular moieties, e.g., hemoglobin, and subjecting the composition to tangential flow filtration (TFF) to separate RBC membrane from the non-membrane cellular moieties, e.g., hemoglobin.

RBC membrane coated nanoparticles, e.g., human RBC membrane coated nanoparticles, which contain inner cores comprising a non-cellular material, e.g., poly(lactic-co-glycolic acid) (PLGA), are referred to as nanosponges or NS. The nanosponges are generally prepared according to the principles or procedures described in US 2013/337066 A1 or WO 2017/087897 A1 as well. For example, RBC membrane coated nanoparticles can be prepared by a process that comprises the steps of mixing a nanoparticle inner core comprising a non-cellular material, e.g., PLGA, with cellular membranes derived from red blood cells using a high shear fluid processor to form a nanoparticle comprising the inner core and an outer surface comprising the RBC cellular membrane. The high shear fluid processor can be a microfluidizer (or a microfluidizer processor).

Test and Control Articles

Test and Control Articles include: human TFF RBC membranes: MA71, MA72; human Nanosponge: NS76; anti-human Band 3 antibody, Sigma, Cat #SAB4200722; SimpleBlue SafeStain (ThermoFisher Cat #LC6065); and Fixation solution: Methanol:Acetate:H2O=50:10:40.

Test and Control Articles

Two human RBC membrane were prepared and submitted to Proteomics Facility at Michigan State University (MSU) to perform a LC/MS/MS proteomics analysis. To develop a quantification method to trace down human nanosponge, Bioanalytical Chemistry at Charles River Laboratories—Ashland performed an analytical development to determine amount of the human Band 3 protein in the samples that human nanosponge spiked into cynomolgus monkey (*Macaca fascicularis*) plasma using LC/MS/MS proteomics. The equipment is Thermo Q-Exactive that targeted MS2.

Procedures

Human RBC Membrane Proteome

To determine the human RBC membrane proteome, the human RBC membrane preparations were subjected to run into SDS-PAGE for 10 minutes and gel were sliced and submitted to Proteomics Facility at Michigan State University (MSU) to perform a LC/MS/MS proteomics analysis.

Human Band 3 Protein does not Present in Human Plasma

Human Band 3 protein is abundant in the human RBC membrane proteome study. To show it can be used to monitor nanosponge in PK/TK studies, a western blot was performed over the samples on human nanosponge, RBC membrane, human and animal plasma using anti-human Band 3 antibody (Sigma, Cat #SAB4200722) to determine whether Band 3 protein exists in the human or animal plasma preparations. (FIG. 2)

Human Band 3 Protein can be Traced in Mouse Plasma after Human Nanosponge Injection Intravenously To further show that Band 3 protein can be traced in human and animal PK/TK studies, we introduced human nanosponge into mice intravenously and determined the level of Band 3 protein in mouse plasma after 5 minutes and 60 minutes of injection with western blot. (FIG. 3)

Human Band 3 Protein Quantification in Nanosponge Spiked Cynomolgus Monkey Plasma To further implement an analytical method for PK studies in cynomolgus monkey to trace down human nanosponge in cynomolgus monkey plasma, Bioanalytical Chemistry at Charles River laboratories—Ashland developed an LC/MS/MS proteomics method to trace down and quantify human Band 3 protein/peptide when human nanosponge is spiked into the cynomolgus monkey plasma.

Calculations and Statistical Methods

Mascot parameters for all databases were as follows:

- allow up to 2 missed tryptic sites
- Fixed modification of Carbamidomethyl Cysteine,
- variable modification of Oxidation of Methionine, Deamidation of Asparagine and Glutamine
- peptide tolerance of +/−10 ppm
- MS/MS tolerance of 0.3 Da
- FDR calculated using randomized database search.

Results

Human RBC Membrane Proteome

Two human RBC membrane preparations, MA71 and MA72, were made and submitted to Proteomics Facility at Michigan State University (MSU) to perform a LC/MS/MS proteomics analysis. The results of the proteome on RBC membrane protein can be viewed and presented in Scaffold View 4.7.3 (http://www.proteomesoftware.com). FIG. 1 is a screen shot of total spectrum count on the condition of 1% FDR protein threshold with minimal two peptides matched of human RBC proteins in all three submitted samples. The structure and membrane proteins of ankryin-1, spectrin alpha and beta, band 3 anion transport protein, hemoglobin alpha and beta, erythrocyte membrane protein 4.1, 4.2, erythrocyte band 7 integral membrane protein, tropomysin, carbonic anhydrase, glucose transport carrier protein etc. are among the top hits. (FIG. 1)

Human Band 3 Protein is Uniquely Present in Human RBC Membrane, not in Human Plasma/Serum Human RBC proteome studies determined that Band 3 protein, Spectrin alpha, beta and ankyrin-1 are the most abundant proteins in the nanosponge. To show that human Band 3 protein can be used for trace down nanosponge product using either LC/MS/MS proteomics or ELISA methods, it has to be not present in the human plasma context. We performed a western blot using anti-human Band 3 specific antibody (Sigma, Cat #SAB4200722). FIG. 2 shows that human band 3 is uniquely presented in the RBC membrane, not in animal plasma and can be used for trace down nanosponge product for PK/PD/TOX studies.

Human Band 3 Protein can be Traced in Mouse Plasma after Human Nanosponge Injection by Western Blot To further show that Band 3 protein can be traced in human and animal PK/TK studies, we introduced human nanosponge into mice intravenously and determined the level of Band 3 protein in mouse plasma after 5 minutes and 60 minutes of injection with western blot. FIG. 3 shows that human Band 3 protein can be used to trace nanosponge injected into mice.

Human Band 3 Protein is not Present in the Plasma Proteome Database (http://plasmaproteomedatabase.org/)

Plasma Proteome Database (PPD, http://plasmaproteomedatabase.org/) was developed as a part of Human Proteome Organization's (HUPO) initial effort to characterize human plasma proteome. This is one of the largest resources on proteins reported in plasma and serum. PPD hosts qualitative and quantitative information on proteins (including those from MRM-based assays) reported in plasma and serum and hence serves as reference platform for biomarker discovery. In addition, proteins reported in extracellular vesicle isolated from plasma are also available. PPD query interface is designed to facilitate individual and batch queries using gene symbols, PubMed identifiers, RefSeq accessions, UniProt IDs or peptide sequences. Each of the protein is linked to external resources such as Entrez Gene, Human Protein Reference Database (HPRD), UniProt and NetPath for more details.

Searching through Plasma Proteome Database, Band 3 protein is not on the list, further prove the uniqueness of the Band 3 protein in RBC membrane. Although spectrin alpha, beta and ankyrin-1 were in the list of the database, however, the amount of the quantification result are in the level of 1.2-1.8 ng/ml. FIG. 4 shows the example of ankyrin-1 listed in the Plasma Proteome Database. It is important to note that although spectrin alpha, beta and ankyrin-1 were in the list of the database, they were only reported by Liu et al (2007) and Farrah et al (2011), and quantification is in a very low amount. With that amount of low quantity (1.2-1.8 ng/ml) of spectrin alpha, beta and ankyrin-1 in human plasma, they can be the good candidates for trace down human nanosponge using LC/MS/MS proteome or specific antibodies ELISA.

Human Band 3 Protein can be Quantified in Nanosponge Spiked Cynomolgus Monkey Plasma To further implement an analytical method for our PK studies in cynomolgus monkey to trace down human nanosponge in cynomolgus monkey plasma, Bioanalytical Chemistry at Charles River laboratories—Ashland developed an LC/MS/MS proteomics method to trace down and quantify human Band 3 protein/peptide when spiked human nanosponge into the cynomolgus monkey plasma. Five signature peptides were used to monitor the level of hNS in Monkey plasma. The digestion will be repeated with acid cleavable detergents to avoid possible ion suppression. These also might enhance the digestion. The spiked standard will be precipitated to remove all of the core material of the nano-particle. This might increase signal. The digestion with acid cleavable detergents yielded multiple Band 3 peptides with detection limits of 25 μg/mL with full scan MS in monkey plasma. MS/MS are being run to improve the LLOQ. It is likely the LLOQ will be 2.5-5 μg/ml in term of nanosponge product.

REFERENCES

Certain References are listed below.

Farrah T, Deutsch E W, Omenn G S, Campbell D S, Sun Z, et al. A high-confidence human plasma proteome reference set with estimated concentrations in Peptide Atlas. *Mol Cell Proteomics*. 2011; 10(9):M110.006353.

Liu X, Valentine S J, Plasencia M D, Trimpin S, Naylor S, Clemmer D E. Mapping the human plasma proteome by SCX-LC-IMS-MS. *J Am Soc Mass Spectrom*. 2007; 18(7):1249-64.

Goodman, S R, Krebs K E, Whitfield C F, Riederer B M, and Zagon I S. Spectrin and related molecules. *Crit. Rev. Biochem*. 1988; 23, 171-234.

Pennell R B. In: Surgenor D M, editor. *The red blood cell*. New York: Academic Press; 1974. p. 93-146.

Kakhniashvili D G, Bulla Jr L A. and Goodman S R. The Human Erythrocyte Proteome Analysis by Ion Trap Mass Spectrometry. *Molecular & Cellular Proteomics*, 2004; 3: 501-509.

Pasini E M, Kirkegaard M, Mortensen P, Lutz H U, Thomas A W. and Mann M. In-depth analysis of the membrane and cytosolic proteome of red blood cells. *Blood* 2006; 108: 791-801.

Pasinia E M, Lutz H U, Mannc M, Thomas A W. Red blood cell (RBC) membrane proteomics Part I: Proteomics and RBC physiology *Journal of Proteomics* 2010; 73 (3): 403-420.

Pasini E M, Lutz H U, Mann M, Thomas A W. Red blood cell (RBC) membrane proteomics—Part II: Comparative proteomics and RBC patho-physiology. *J Proteomics*. 2010; 73(3):421-35.

Shevchenko, A., Wilm, M., Vorm, O., Mann, M. Mass spectrometric sequencing of proteins silver-stained polyacrylamide gels. *Anal Chem*. 1996; 68(5): 850-8.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for monitoring a cellular membrane coated nanoparticle after in vivo administration, which method comprises:

a) obtaining a sample from a subject to which has been administered a cellular membrane coated nanoparticle, said nanoparticle comprising an inner core comprising a non-cellular material and an outer surface comprising a cellular membrane derived from a cell; and b) assessing the presence, absence, amount and/or level of a biomarker from cellular membrane of said cellular membrane coated nanoparticle in said sample, said biomarker having a base level in said sample that is below a threshold level, and wherein said biomarker is Band 3 protein, or a fragment thereof, and a ratio between said level of said biomarker in said sample obtained from said subject to which has been administered said nanoparticle and said base level of said biomarker in said sample is at least 2, and said method has an assay linearity ranging from 100 pg Band 3 protein/ml sample to 100 ng Band 3 protein/ml sample, a relative standard deviation (RSD) of 30% or less, and a limit of detection (LOD) of Band 3 protein at about 50 pg or 100 pg Band 3 protein/ml sample.

2. The method of claim 1, wherein the sample is a bodily fluid from a subject or an extract from a subject.

3. The method of claim 1, wherein the mammal is a human or a non-human mammal.

4. The method of claim 1, wherein the inner core of the nanoparticle supports the outer surface of the nanoparticle.

5. The method of claim 1, wherein the cellular membrane of the nanoparticle is derived from a blood cell, a tumor cell, a cancer cell, an immune cell, a stem cell, an endothelial cell, an exosome, a secretory vesicle or a synaptic vesicle.

6. The method of claim 5, wherein the cellular membrane comprises a plasma membrane derived from a red blood cell.

7. The method of claim 1, wherein the nanoparticle has a diameter from about 10 nm to about 10 μm.

8. The method of claim 1, wherein the nanoparticle substantially lacks constituents of the cell from which the cellular membrane is derived.

9. The method of claim 1, wherein the nanoparticle substantially maintains natural structural integrity or activity of the cellular membrane or the constituents of the cellular membrane.

10. The method of claim 1, wherein the nanoparticle is biocompatible or biodegradable.

11. The method of claim 1, wherein the nanoparticle substantially lacks immunogenicity to a species or subject from which the cellular membrane is derived.

12. The method of claim 1, wherein the presence, absence and/or amount of a biomarker is assessed by an immunoassay, a chromatography analysis, a mass spectrometry analysis, a proteomics analysis, or a combination thereof.

13. The method of claim 12, wherein the presence, absence and/or amount of a biomarker is assessed by liquid chromatography-mass spectrometry (LC/MS) analysis or liquid chromatography-mass spectrometry-mass spectrometry (LC/MS/MS) analysis.

14. The method of claim 1, wherein the cellular membrane in the nanoparticle is derived from a cell of a species that is the same as that of the subject to which the nanoparticle has been administered.

15. The method of claim 1, which is used to monitor the nanoparticle in a quality control (QC) test or quality assurance (QA) test.

16. The method of claim 1, which is used to monitor the nanoparticle in a pharmacology study or in a toxicology study.

17. The method of claim 1, wherein a ratio between the level of a biomarker in a sample obtained from a subject to which has been administered the nanoparticle and the base level of the biomarker in the sample is at least 3.

18. The method of claim 1, which further comprises administering the cellular membrane coated nanoparticle to the subject.

19. The method of claim 2, wherein the bodily fluid from a subject is a blood, plasma, serum, saliva or urine sample from the subject.

20. The method of claim 1, which is used to monitor the nanoparticle in a process for manufacturing or inspecting the nanoparticle.

* * * * *